United States Patent
Pell

(10) Patent No.: US 8,927,083 B2
(45) Date of Patent: Jan. 6, 2015

(54) HANDLE AND METHOD OF FABRICATING A HANDLE FOR A MEDICAL DEVICE

(75) Inventor: Randolph W. Pell, Marlboro, VT (US)

(73) Assignee: Mack Molding Company, Arlington, VT (US)

( * ) Notice: Subject to any disclaimer, the term of this patent is extended or adjusted under 35 U.S.C. 154(b) by 964 days.

(21) Appl. No.: 12/356,013

(22) Filed: Jan. 19, 2009

(65) Prior Publication Data

US 2010/0180400 A1   Jul. 22, 2010

(51) Int. Cl.
| | |
|---|---|
| B32B 3/00 | (2006.01) |
| A47B 95/02 | (2006.01) |
| B25G 1/00 | (2006.01) |
| B25G 1/10 | (2006.01) |
| B29C 45/16 | (2006.01) |
| A61B 17/00 | (2006.01) |
| A61B 19/00 | (2006.01) |
| B29L 31/46 | (2006.01) |
| B29L 31/00 | (2006.01) |

(52) U.S. Cl.
CPC .............. *B25G 1/10* (2013.01); *B29C 45/1676* (2013.01); *A61B 2017/0042* (2013.01); *A61B 2017/00526* (2013.01); *A61B 2019/446* (2013.01); *B29K 2995/0025* (2013.01); *B29K 2995/0026* (2013.01); *B29L 2031/463* (2013.01); *B29L 2031/753* (2013.01); *Y10S 606/907* (2013.01); *Y10S 606/91* (2013.01)
USPC ............. 428/68; 428/161; 428/172; 428/187; 428/203; 606/907; 606/910; 81/489; 74/551.9; 74/558.5; 16/110.1

(58) Field of Classification Search
USPC ........... 428/68, 161, 172, 187, 203; 16/110.1; 81/489; 74/551.9, 557, 558.5; 362/572; 604/534; 606/907, 910
See application file for complete search history.

(56) References Cited

U.S. PATENT DOCUMENTS

| | | | | |
|---|---|---|---|---|
| 2,451,913 | A | * | 10/1948 | Brice .............................. 428/67 |
| 4,830,892 | A | * | 5/1989 | Nussbaum ..................... 428/31 |
| 4,949,457 | A | | 8/1990 | Burout, III |
| 5,711,720 | A | | 1/1998 | Janes et al. |
| 5,857,241 | A | | 1/1999 | Camp, Jr. et al. |
| 5,920,943 | A | | 7/1999 | Barker |
| 6,024,903 | A | | 2/2000 | Naft et al. |
| 6,195,830 | B1 | | 3/2001 | Bruschi |
| 6,202,598 | B1 | | 3/2001 | Willinger |
| 6,264,869 | B1 | * | 7/2001 | Notarpietro et al. .......... 264/247 |
| 6,322,362 | B1 | | 11/2001 | Holms |

(Continued)

FOREIGN PATENT DOCUMENTS

EP   330870 A3   9/1989

*Primary Examiner* — Donald J Loney
(74) *Attorney, Agent, or Firm* — Heslin Rothnberg Farley & Mesiti P.C.

(57) ABSTRACT

A handle and a method of fabricating a handle, or another article of manufacture, that minimizes or avoids the likelihood of accumulating contamination before, during, or after use. The article includes a core element, for example, a plastic core element, having an outer surface and raised indicia, such as, letters or logos, extending beyond the outer surface; and a light-transferring material completely covering the raised indicia of the core element wherein the raised indicia are visible through the light-transferring material. The complete covering of the indicia avoids separation between the cover and the indicia. The cover material may be a translucent thermoplastic elastomer. Though particularly applicable to the medical device industry, aspects of the invention may be applied to a broad range of industries.

35 Claims, 5 Drawing Sheets

(56) References Cited

U.S. PATENT DOCUMENTS

| | | |
|---|---|---|
| 6,726,868 B1 | 4/2004 | Panfili et al. |
| 6,749,788 B1 | 6/2004 | Holden et al. |
| 6,749,790 B1 | 6/2004 | Lieser et al. |
| 6,779,937 B1 | 8/2004 | Lombardi et al. |
| 7,195,567 B2 * | 3/2007 | Lu ................................ 473/300 |
| 7,325,469 B1 * | 2/2008 | Clampitt et al. ............... 81/436 |
| 7,461,474 B1 * | 12/2008 | Lu et al. ......................... 40/660 |
| 2003/0070259 A1 | 4/2003 | Brown et al. |
| 2004/0121671 A1 | 6/2004 | Skedeleski |
| 2004/0224786 A1 | 11/2004 | Reardon |
| 2007/0031595 A1 | 2/2007 | Fox |
| 2007/0186453 A1 | 8/2007 | Little et al. |
| 2008/0014412 A1 | 1/2008 | Hortnagl et al. |
| 2008/0102974 A1 | 5/2008 | Nam et al. |

* cited by examiner

HANDLE AND METHOD OF FABRICATING A HANDLE FOR A MEDICAL DEVICE

BACKGROUND OF THE INVENTION

1. Field of the Invention

The present invention generally relates to articles of manufacture and methods of fabricating those articles, for example, handles. More particularly, the present invention relates handles, for example, handles for medical devices, and methods of fabricated handles having a core with human readable indicia and a translucent cover through which the indicia can be read.

2. Description of Related Art

In the art of medical devices, there are many types of handles and handle-like structures formed by molding and over molding, for example, molding a first material over a second or core material. Often, some form of logo or insignia is provided on the core material that is exposed, and thus viewable, after over molding. This is typically achieved by providing an over molded material having and outer surface that is substantially tangent to the surface of the logo or insignia. However, since the core material and the over molded material are typically of different composition, the interface between the over molded material and the logo or insignia is susceptible to separation. Typically, such separation can provide an ideal location for dirt and microbes to congregate and spread. Clearly, a need exists in the art to avoid such separations, especially, in the field of medical devices.

The prior art discloses various handle structures having over molded logos or insignia. For example, U.S. Pat. No. 6,749,790 issued to Lieser, et al. discloses a handle formed from a shank over molded with a core of a polypropylene and then over molded with a thermoplastic elastomer. U.S. Pat. No. 6,726,868 issued to Panfili, et al. discloses a double molding process for producing a "sign" or logo in a handle. U.S. Published Patent Application No. 2007/0186453 A1 issued to Little, et al. discloses a toothbrush that has a thermoplastic elastomer molded to a handle and completely seals an image pocket. U.S. Published Patent Application No. 2004/0121671 A1 issued to Skedeleski discloses a fin construction having registration posts for over molding a flexible material. U.S. Pat. No. 6,195,830 issued to Bruschi discloses a paintbrush handle having a core over molded with a soft thermoplastic rubber and having a raised part that penetrates the rubber. However, though these and other prior art references disclose some form of over molding about a structure, the structure or indicia over molded is invariably covered by the over molded material. That is, as is typical of the prior art, the over mold material simply abuts, and does not seal, whatever is projecting from the core of the handle.

However, none of the prior art discloses an over molded article construction with encapsulated logo or insignia that avoids the undesirable separation discussed above. Aspects of the present invention address this and other limitations of the prior art.

SUMMARY OF THE INVENTION

According to aspects of the present invention articles of manufacture and methods of fabricated articles of manufacture, for example, medical device handles, are provided which avoid or prevent the undesirable separation of the over molded material from the logo or insignia by substantially completely covering the logo or insignia on the core with a translucent material. As a result, the logo or insignia is visible through the translucent material without providing interfaces that may separate between the over molded material and the logo or insignia.

One aspect of the invention is a method for fabricating an article, for example, a handle, the method comprising or consisting of providing a core element having an outer surface and raised indicia extending beyond the outer surface; and molding a light-transferring material over the raised indicia of the core element wherein the light-transferring material completely covers the raised indicia, and wherein the raised indicia are visible through the light-transferring material. The raised indicia may be raised letters, numerals, symbols, characters, designs, logos, pictures, decorations, or a combination thereof. In one aspect the light-transferring material, for example, a translucent or transparent material, may completely cover the raised indicia wherein no gaps are provided on an outer surface of the article between the raised indicia and the light-transferring material. The light transferring material may typically be an elastomeric material having a softening point of at least about 100 degrees C., for example, a translucent GLS Kraton® thermoplastic elastomer, or its equivalent.

Another aspect of the invention is an article of manufacture, for example, a handle, comprising or consisting of: a core element having an outer surface and raised indicia extending beyond the outer surface; and a light-transferring material completely covering the raised indicia of the core element wherein the raised indicia are visible through the light-transferring material. Again, the raised indicia may be one or more of the indicia described above. In one aspect, the light-transferring material completely covers the raised indicia wherein no gaps are provided on an outer surface of the article between the raised indicia and the light-transferring material. Again, the light-transferring material on this article may be a translucent and a transparent material, for example, a translucent thermoplastic elastomer, such as, GLS Kraton® thermoplastic elastomer.

These and other aspects, features, and advantages of this invention will become apparent from the following detailed description of the various aspects of the invention taken in conjunction with the accompanying drawings

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention will be readily understood from the following detailed description of aspects of the invention taken in conjunction with the accompanying drawings in which:

DETAILED DESCRIPTION

Figure 1:
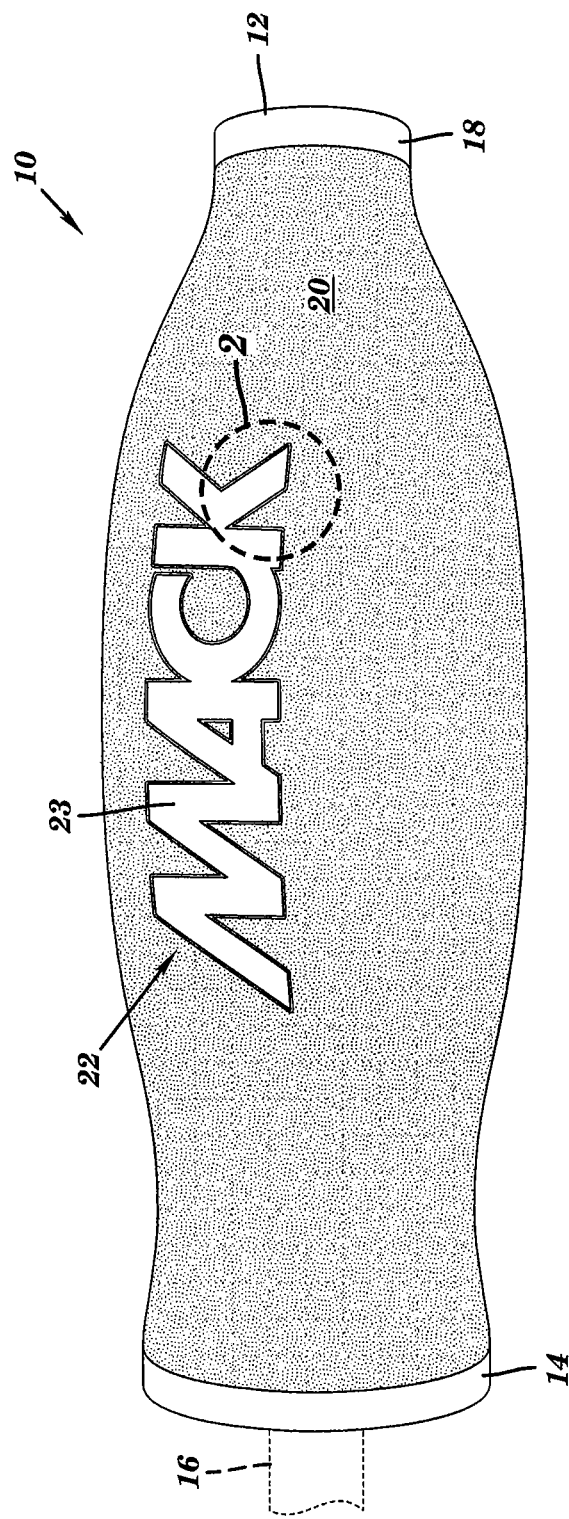
FIG. 1 is a perspective view of a handle for a medical device according to the prior art.

FIG. 1 is a perspective view of a handle 10 for a medical device according to the prior art. As is typical of the prior art, handle 10 comprises an elongated member adapted to be grasped and manipulated by the user, for example, the surgeon. Handle 10 typically has a first, free end 12 and a second end 14 to which a tool shaft 16 (a representative portion of which is shown in phantom) is typically mounted, for example, a surgical boring tool and the like. The handle 10 typically comprises an elongated core element 18 shaped and contoured to facilitate handling. In order to enhance the users grasp of the handle 10, core element 18 may be covered, for example, over molded, with a cover 20, for example, a cover made of an elastomeric material having increased frictional properties, that is, typically increased frictional properties compared to the material of core 18. The material of cover 20 may be, for example, a thermoplastic elastomer or a thermoplastic polyurethane. The cover 20 typically enhances the grippability of tool 10.

In addition, it is common for marketing information or indicia 22 to be provided on handle 10, for example, the name of the handle manufacturer or the name of the facility at which tool 10 is used. As is typical, as in the case shown in FIG. 1, the indicia 22 are provided as raised letters on the surface of the core 18. The raised indicia 22 are then typically over molded with cover 20 whereby the surface of the raised indicia 22 and the surface of the over molded cover 20 are substantially co-planar. In other words, raised indicia 22 typically penetrate cover 20 and the surface 23 of indicia 22 are exposed to the external environment. Though such exposed over molded indicia may provide enhanced definition or visibility to the indicia 22, the penetration of cover 20 by indicia 22 can have undesirable disadvantages, especially when handle 10 used as a medical device.

Figure 2:
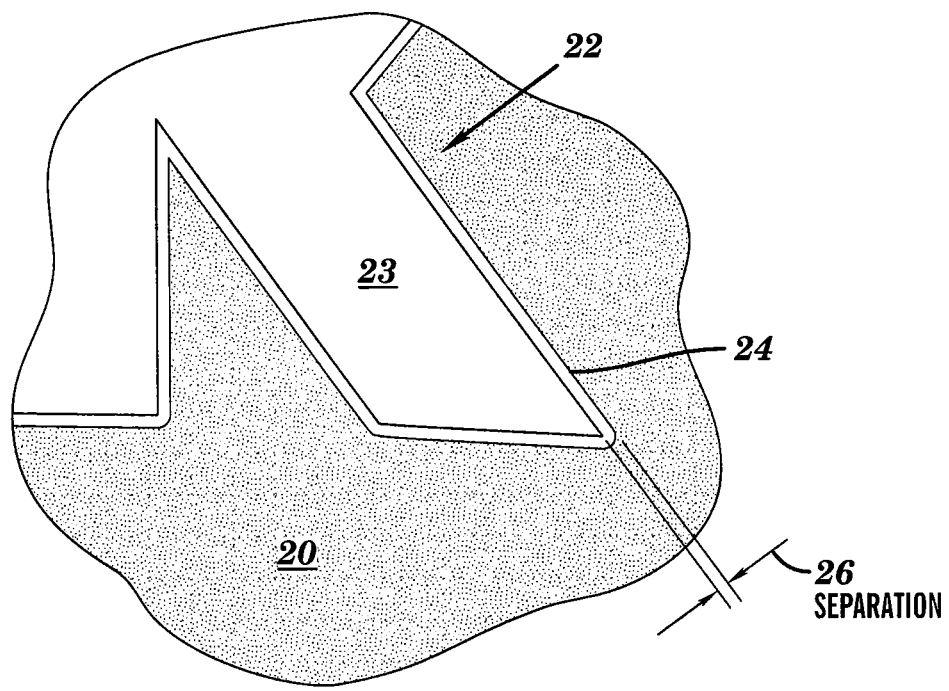
FIG. 2 is a perspective view of a detail of the prior art handle shown in FIG. 1 identified by Detail 2 in FIG. 1.

FIG. 2 is a perspective view of a detail of the prior art handle 10 shown in FIG. 1 identified by Detail 2 in FIG. 1. As shown in FIG. 2, since indicia 22 penetrate through cover 20, an interface 24 between indicia 22 and cover 20 is typically present. Because the core 18 (typically, harder and more rigid) and cover 20 (typically, softer and more pliable) are typically of different materials, there is typically no bonding between the cover 20 and the indicia 22 at interface 24. Since the interface 24 is typically not bonded, one or more separations 26 between indicia 22 and cover 20 are often encountered on over molded handles having raised indicia. The separation 26 can be exacerbated by repeated handling, for example, by the surgeon, and due to the extreme temperature variations the handle 10 is typically exposed to, for example, during high temperature sterilization. However, the undesirable disadvantage of separation 26 is the potential home separation 26 can proved for undesirable substances or organisms. For example, such crevices provided by separation 26 can be ideal locations for microbes to gather and propagate. This is especially true in hospital environments in which medical devices having these prior art handles are typically used. Of course, separation 26 in FIG. 2 is only a representative separation identified for the sake of this disclosure. Interface 24 is present wherever cover 20 abuts a character or image of indicia 22 and separation 26, and its potential to accumulate germs and bacteria, may be found anywhere and everywhere along interface 24 of handle 10. Aspects of the present invention, address this undesirable limitation, among others, of the prior art.

Figure 3:
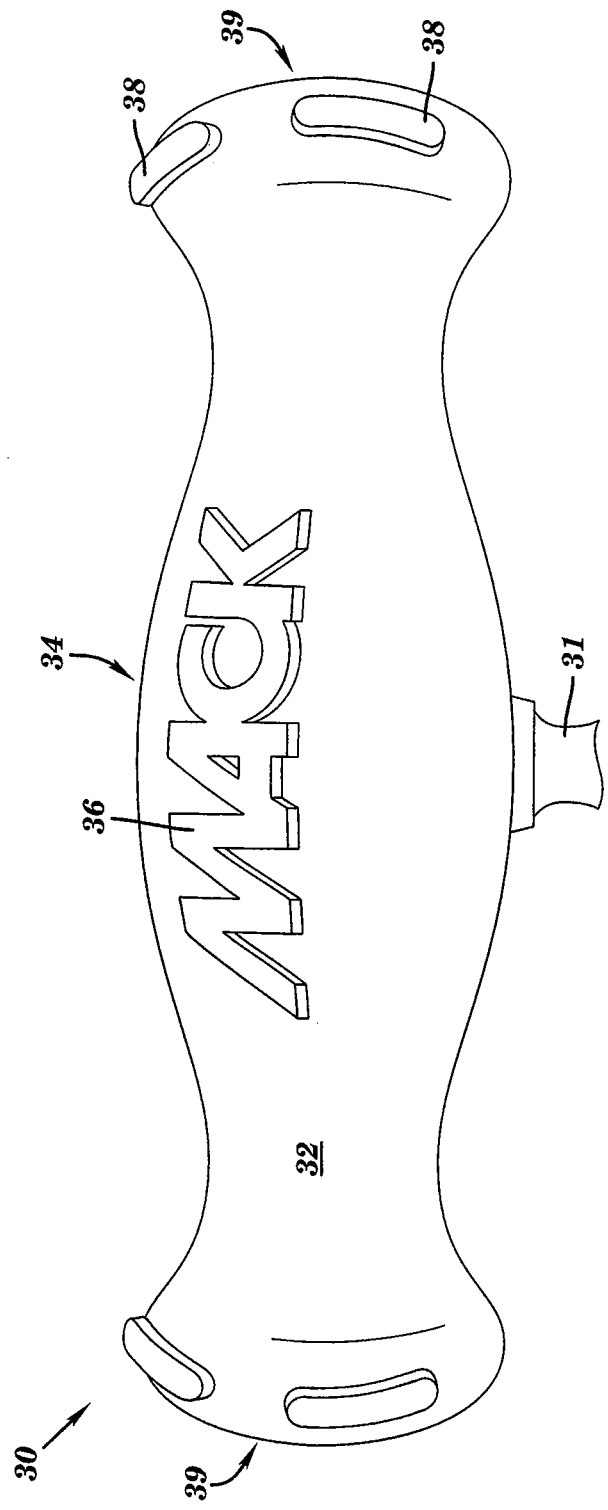
FIG. 3 is perspective view of core element prior to over molding according to one aspect of the invention.
Figure 5:
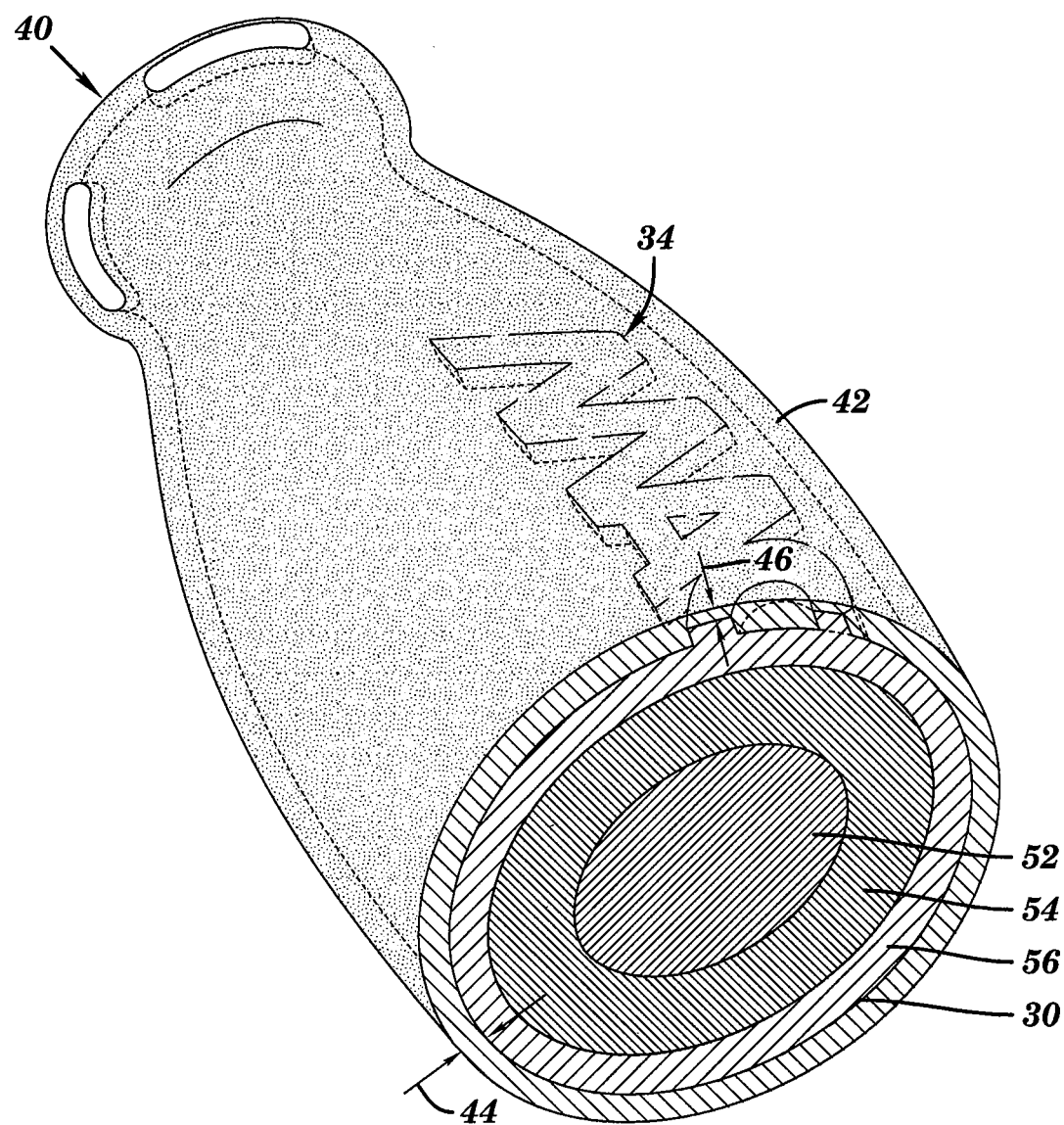
FIG. 5 is a perspective, cross-sectional view of the handle shown in FIG. 4 as sectioned along lines 5-5 in FIG. 4.

FIG. 3 is perspective view of core element 30 prior to over molding according to one aspect of the invention. Core element 30 may be metallic or non-metallic, including plastic or wood, but core element 30 is typically made from a plastic or a plastic mounted on a metallic inner core, as shown in FIG. 5. In one aspect, core element 30 may be made from a polypropylene, a polycarbonate, or a acrylonitrile butadiene styrene (ABS), for example, injection molded from a polypropylene or a polycarbonate. Core element 30 may also be shaped to provide comfort and compatibility with the grasp of the user, including ridges and bulbous ends to facilitate handling by the user.

As shown in FIG. 3, elongated, uncovered core element 30 may typically include a tool shaft 31 projecting from core element 30 and having a tool end or adapted to receive a tool. Though in FIG. 3, tool shaft 31 projects radially about a centerline of core element 31, one or more tool shafts 31 may project from anywhere along core element 31, including projecting axially from an end of core element 31 as shown by tool shaft 16 in FIG. 1.

According to aspects of the invention, core element 31 typically comprises an outer surface 32 and raised indicia 34 that extend beyond the outer surface 32 of core element 30 and provide one or more surfaces 36 above the surface of outer surface 32. As used in this specification and claims the term "indicia" refers to any mark intended to convey information to the viewer. For example, indicia may include letters, numerals, symbols, characters, designs, logos, pictures, decorations, or combinations thereof, among other means of relaying information to the viewer. As also shown in FIG. 3, core element 30 may also include one or more additional areas 38 having raised surfaces, that is, areas raised above the surface of surface 32, that, as will be discussed below, may provide a retention mechanism for the cover of handle 30. As shown in FIG. 3, additional raised areas 38 may be positioned on bulbous ends 39 of core element 30.

Figure 4:
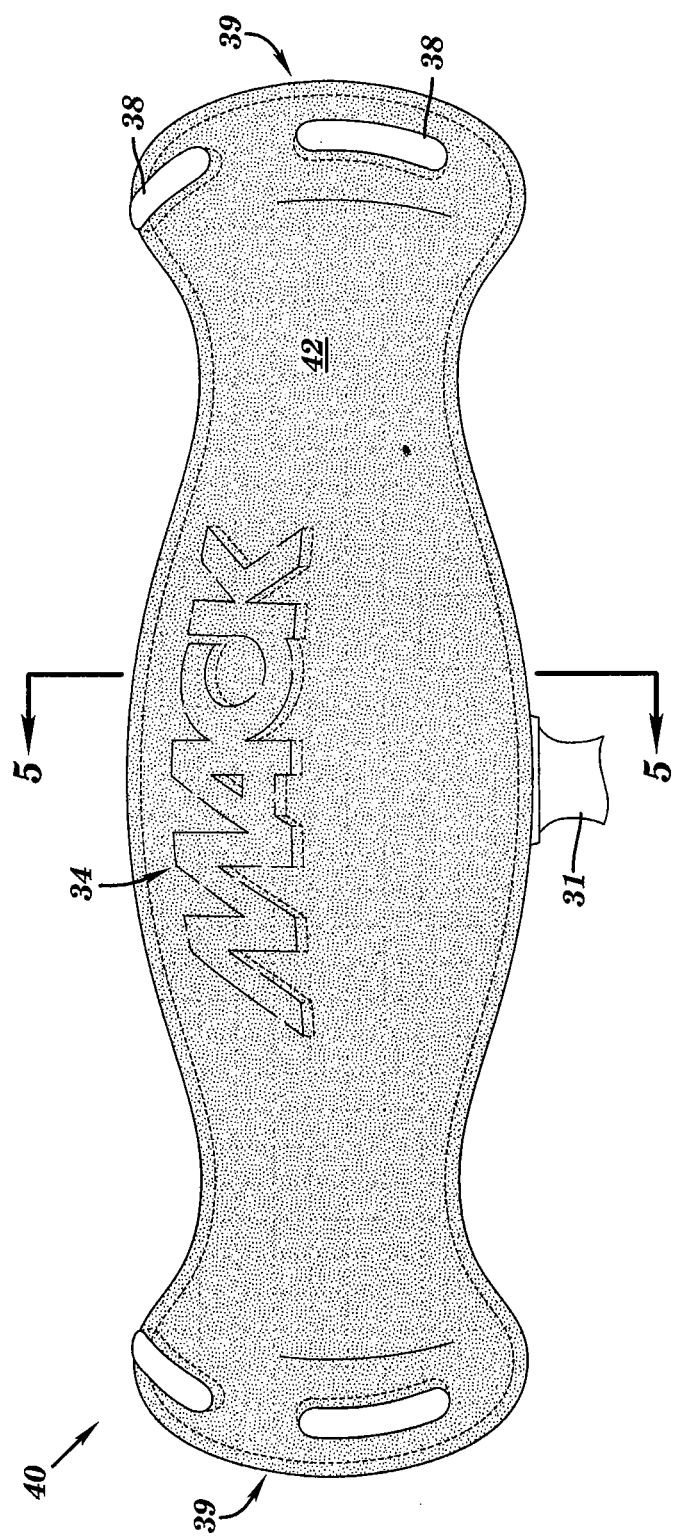
FIG. 4 is a perspective view of a handle according to an aspect of the present invention after over molding the core element shown in FIG. 3.

FIG. 4 is a perspective view of a handle 40 according to an aspect of the present invention after over molding the core element 30 shown in FIG. 3 with a material or cover 42. According to aspects of the invention, cover 42 may comprise an elastomeric material, for example, to provide a resilient, comfortable grip, having enhanced friction that resists slippage from the user's hand, for example, when exposed to blood or another bodily fluid during surgery. The elastomeric material may be a light-transferring material, that is, material that may be at least partially translucent, for example, through which indicia 34 may be at least partially visible. In addition, in one aspect of the invention, the elastomeric may have a softening point above the temperature handle 40 is typically exposed to, for example, a softening point of at least 100 degrees C., but may have a softening point above 150 degrees C. or 200 degrees C. When handle 40 is used on a medical device, in one aspect, the elastomeric material from which cover 42 is made may have a softening point temperature greater than at least 250 degrees C., that is, greater than the temperature a medical device is likely to be exposed to during sterilization, for example, in an autoclave or similar sterilization device. In another aspect, the elastomeric material from which cover 42 is made may have a softening point temperature greater than at least 300 degrees C.

In one aspect, cover 42 may comprise a thermoplastic elastomer (TPE) (also known as thermoplastic rubbers). Typical TPEs that may be used for cover 42 include, but are not limited to, Styroflex® styrene-butadiene copolymer provided by BASF, Kraton® TPE provided by GLS, Pellethane™ polyurethane provided by Dow Chemical, Pebax® polyether block amide provided by Arkema, Arnitel copolyester provided by DSM, and Hytrel polyester provided by Du Pont, or their equivalents. According to aspects of the invention, the material from which cover 42 is made may typically be at least somewhat translucent whereby indicia 34 may be at least partially visible through the cover. In one aspect, the material of cover 42 may be substantially translucent, and may be substantially transparent, whereby indicia 34 may clearly be seen through cover 42. Cover 42 may include a shade or coloring, for example, a translucent blue or translucent red, among other translucent colorings. In one aspect of the invention, a translucent or transparent grade of GLS Kraton® TPE may be used for cover 42, for example, GLS's G2705 TPE, or its equivalent.

As shown in FIG. 4, and contrary to the prior art, indicia 34 on core element 30 do not penetrate the surface of cover 42. That is, contrary to the prior art, no interfaces between the indicia 34 and the cover 42 are present, for example, no interfaces 24 in FIG. 2 that are susceptible to separation 26 are present in handle 40. Accordingly, according to aspects of the invention, handle 40 may be devoid of and unlikely to obtain any separations 26 that can be locations where microbes can accumulate and propagate. That is, aspects of the present invention provide a marked sanitary improvement over existing handle structures, especially for handles for medical devices.

FIG. 4 also illustrates raised areas 38, for example, on bulbous ends 39, of handle 40. According to one aspect, of the invention, raised areas 38 may be provided that project above the surface 32 of core element 30 and which are not covered by cover 42. In one aspect, raised areas 38 may be positioned anywhere along handle 40 to provide an obstruction to the movement of cover 42 with respect to core element 30. For example, in one aspect, raised areas 38 have a height that is about equal to the thickness of cover 42. Raised areas 38 may also be slightly higher or lower than the thickness of cover 42 whereby raised areas 38 project beyond cover 42 or are recessed below the surface of cover 42. In one aspect, no raised areas 38 are present to minimize or eliminate any possible separation of cover 42 from a raised area 38.

FIG. 5 is a perspective, cross-sectional view of handle 40 shown in FIG. 4 as sectioned along lines 5-5 shown in FIG. 4. FIG. 5 includes a cross-section of core element 30, cover 42, and raised indicia 34 according to one aspect of the invention. As shown, cover 42 may have a thickness 44, which may range from about 0.010 inches to about 0.25 inches, but is typically between about 0.040 inches and about 0.180 inches, for example, between about 0.080 inches and about 0.130 inches. As also shown in FIG. 5, thickness 46 of cover 42 above the height of raised indicia 34 may range from about 0.010 inches to about 0.25 inches, but is typically between about 0.020 inches and about 0.120 inches, for example, between about 0.030 inches and about 0.080 inches.

As shown in FIG. 5, core element 30 may comprise a plurality of components, for example, an inner core 52, an intermediate layer 54, and an outer layer 56 providing the outer surface 32 of core 30. Inner core 52 may be metallic, for example, steel, stainless steel, aluminum, or titanium, among other metals, or plastic, for example, one or more of the plastics disclosed herein. Inner core 52 may provide the structural rigidity typically required for a handle, and may be adapted to receive tool shaft 31 shown in FIG. 3. Intermediate layer 54 may also be a plastic, for example, one or more of the plastics disclosed herein, but may typically be made from a polypropylene, a polycarbonate, or an acrylonitrile butadiene styrene (ABS). Outer layer 56 may also be a plastic, for example, a polypropylene, a polycarbonate, or an ABS. In one aspect, intermediate layer 54 and outer layer 56 may be made of the same material, for example, be both made from a polycarbonate. Moreover, intermediate layer 54 and outer layer 56 may not be separate components, but may comprise a single component made of one material, for example, a polycarbonate.

In one aspect of the invention, a method for fabricating an article, for example, a handle 40 is provided. The method includes or comprises providing a core element 30 having an outer surface 32 and raised indicia 34 extending beyond the outer surface 32; and molding a light-transferring material 42 over the raised indicia 34 of the core element 30 wherein the light-transferring material 42 completely covers the raised indicia 34, and wherein the raised indicia 34 are visible through the light-transferring material 42. In one aspect, the light-transferring material 42 completely covers the raised indicia 34 wherein no gaps or separations 26 (see FIG. 2) are provided on an outer surface of the article 40 between the raised indicia 34 and the light-transferring material 42.

It will be apparent to those of skill in the art that aspects of the invention provide a article of manufacture, for example, a handle, and method of fabricating articles of manufacture having human readable indicia that are not prone to harboring dirt or microbes by preventing the formation of interfaces that may be prone to separation. Though aspects of the invention may be applied to a broad range of over molded articles of manufacture, including, household products, sporting goods, tools, toys, and the like, it will be apparent that aspects of the invention are especially suitable for the manufacture of articles for medical devices, for example, handles for medical device.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

The invention claimed is:

1. A handle comprising:
   a generally cylindrical core element defining an outer surface and raised indicia extending beyond the outer surface, and the raised indicia having one or more surfaces above the surface of the outer surface;
   an overmolded light-transferring elastomeric material completely covering the raised indicia of the cylindrical core element and providing an outer surface of the handle wherein the raised indicia are visible through the light-transferring material, the overmolded light-transferring elastomeric material providing a resilient comfortable grip having enhanced friction that resists slippage from a user's hand; and
   wherein the overmolded light-transferring elastomeric material comprises a thickness above the height of the raised indicia from about 0.010 inches to about 0.25 inches.

2. The handle as recited in claim 1, wherein the raised indicia comprise one or more of raised letters, numerals, symbols, characters, designs, logos, pictures, and decorations.

3. The handle as recited in claim 1, wherein the light-transferring material completely covers the raised indicia wherein no gaps are provided on an outer surface of the article between the raised indicia and the light-transferring material.

4. The handle as recited in claim 1, wherein the light-transferring material comprises one of a translucent and a transparent material.

5. The handle as recited in claim 1, wherein the light-transferring material comprises an elastomeric material having a softening point of at least about 100 degrees C.

6. The handle as recited in claim 5, wherein the light-transferring material comprises an elastomeric material having a softening point of at least about 200 degrees C.

7. The handle as recited in claim 1, wherein the light-transferring material comprises a thermoplastic elastomeric material.

8. The handle as recited in claim 7, wherein the light-transferring material comprises a translucent thermoplastic elastomeric material.

9. The handle as recited in claim 1, wherein the cylindrical core element comprises a plastic generally cylindrical core element.

10. The handle as recited in claim 1, wherein the handle comprises a medical device handle.

11. The handle as recited in claim 1, further comprising a tool attached to the handle.

12. The handle as recited in claim 11, wherein the tool extends radially from a longitudinal axis of the handle.

13. The handle as recited in claim 11, wherein the tool extends along a longitudinal axis of the handle.

14. The handle as recited in claim 1, wherein the outer surface of the handle comprises a contoured outer surface.

15. The handle as recited in claim 1, wherein the ends of the handle comprise bulbous ends.

16. The handle as recited in claim 1, wherein the light-transferring elastomeric material comprises a thickness in a range from 0.040 inches to about 0.180 inches.

17. The handle as recited in claim 11, wherein the light-transferring elastomeric material comprises a thickness above the height of raised indicia from about 0.020 inches and about 0.120 inches.

18. A medical device handle attachable to a medical tool, the medical device handle comprising:
    a generally cylindrical core element defining an outer surface and raised indicia extending beyond the outer surface, and the raised indicia having one or more surfaces above the surface of the outer surface;
    an overmolded light-transferring elastomeric material completely covering the raised indicia of the cylindrical core element and providing an outer surface of the medical device handle, wherein the raised indicia are visible through the light-transferring elastomeric material, the overmolded light-transferring elastomeric material providing a resilient comfortable grip having enhanced friction that resists slippage from a user's hand;
    wherein no gaps are provided on the outer surface of the medical device handle between the raised indicia and the overmolded light-transferring elastomeric material that can harbor microbes; and
    wherein the overmolded light-transferring elastomeric material comprises a thickness above the height of the raised indicia from about 0.010 inches to about 0.25 inches.

19. The medical device handle as recited in claim 18, wherein the raised indicia provide an obstruction to movement of the elastomeric material with respect to the cylindrical core.

20. The medical device handle as recited in claim 18, wherein the elastomeric material provides enhanced friction to resist slippage from a hand of a surgeon.

21. The medical device handle as recited in claim 18, wherein the cylindrical core element comprises an inner metallic element.

22. The medical device handle as recited in claim 18, wherein the raised indicia comprise one or more of raised letters, numerals, symbols, characters, designs, logos, pictures, and decorations.

23. The medical device handle as recited in claim 18, wherein the light-transferring material comprises one of a translucent and a transparent material.

24. The medical device handle as recited in claim 18, wherein the light-transferring material comprises an elastomeric material having a softening point of at least about 100 degrees C.

25. The medical device handle as recited in claim 18, wherein the light-transferring material comprises a thermoplastic elastomeric material.

26. The medical device handle as recited in claim 18, wherein the cylindrical core element comprises a plastic core element.

27. The medical device handle as recited in claim 18, wherein the light-transferring elastomeric material further substantially completely covers the cylindrical core element.

28. The medical device handle as recited in claim 18, further comprising a tool attached to the medical device handle.

29. The medical device handle as recited in claim 28, wherein the tool extends radially from a longitudinal axis of the medical device handle.

30. The medical device handle as recited in claim 28, wherein the tool extends along a longitudinal axis of the medical device handle.

31. The medical device handle as recited in claim 18, wherein the outer surface of the medical device handle comprises a contoured outer surface.

32. The medical device handle as recited in claim 18, wherein ends of the medical device handle comprise bulbous ends.

33. The medical device handle as recited in claim 18, wherein the light-transferring elastomeric material comprises a thickness in a range from about 0.010 inches to about 0.25 inches.

34. The medical device handle as recited in claim 18, wherein the light-transferring elastomeric material comprises a thickness in a range from 0.040 inches to about 0.180 inches.

35. The medical device handle as recited in claim 18, wherein the light-transferring elastomeric material comprises a thickness above the height of raised indicia from about 0.020 inches and about 0.120 inches.

* * * * *

UNITED STATES PATENT AND TRADEMARK OFFICE
CERTIFICATE OF CORRECTION

PATENT NO. : 8,927,083 B2  
APPLICATION NO. : 12/356013  
DATED : January 6, 2015  
INVENTOR(S) : Pell Page 1 of 1

It is certified that error appears in the above-identified patent and that said Letters Patent is hereby corrected as shown below:

In the Claims

Column 7, Line 22: Claim 17, Delete "claim 11" and insert --claim 1--

Signed and Sealed this
Twelfth Day of May, 2015

Michelle K. Lee
*Director of the United States Patent and Trademark Office*